United States Patent [19]

Farrell et al.

[11] Patent Number: 5,464,744
[45] Date of Patent: Nov. 7, 1995

[54] METHODS AND COMPOSITIONS FOR REDUCING FALSE POSITIVE SIGNALS IN AN RNA AMPLIFICATION SYSTEM

[75] Inventors: Michael P. Farrell, Marlborough; Juili L. Lin-Goerke, Framingham, both of Mass.

[73] Assignee: Norval B. Galloway

[21] Appl. No.: 950,131

[22] Filed: Sep. 24, 1992

[51] Int. Cl.⁶ .............................. C12Q 1/68; C12P 19/30; C07H 21/02
[52] U.S. Cl. .............................. 435/6; 435/91.1; 435/91.2; 435/91.21; 435/91.3; 435/91.32; 435/91.51; 435/193; 435/194; 536/23.1; 536/25.3; 935/3; 935/17; 935/19; 935/77
[58] Field of Search .................................. 435/91, 6, 193, 435/194, 91.2, 91.1, 91.21, 91.3, 91.32, 91.51; 536/23.1, 25.3; 935/3, 17, 19, 77

[56] References Cited

U.S. PATENT DOCUMENTS

| 4,957,858 | 9/1990 | Chu et al. | 435/6 |
| 5,141,857 | 8/1992 | DiFrancesco | 435/91 |

FOREIGN PATENT DOCUMENTS

| 0415755 | 3/1991 | European Pat. Off. . |
| 0430270 | 6/1991 | European Pat. Off. . |
| 0454461 | 10/1991 | European Pat. Off. . |
| WOA89/11548 | 11/1989 | WIPO . |
| WOA90/15135 | 12/1990 | WIPO . |

OTHER PUBLICATIONS

Pritchard et al. (1990) Ann. Biol. Clin., vol. 48, pp. 492–497.
Feix et al. (1967) Proceedings of the Nat'l Acad. of Sciences (USA), vol. 57, No. 5, pp. 1401–1408.
Sumper et al. PNAS 72:162–166, 1975.
Schaffner et al. (1977) J. Mol. Biol., vol. 117, pp. 877–907.
Flanagan et al. (1979) J. of Virology, vol. 29, No. 1, pp. 352–360.
Chifflot et al. (1980) Virology, vol. 100, pp. 91–100.
Lizardi, et al., Trends in Biotech. vol. 9: 53–58 (Feb. 1991).

Primary Examiner—Margaret Parr
Assistant Examiner—Ardin H. Marschel
Attorney, Agent, or Firm—Norval B. Galloway

[57] ABSTRACT

Disclosed herein is a composition comprising ribonuclease treated RNA or DNA dependent RNA polymerase, and the use of same in amplification methods. The treatment of the RNA or DNA dependent RNA polymerase with ribonuclease reduces or eliminates false positives which result from the presence of an endogenous or contaminating replicatable template species in the Qβ replicase enzyme preparation.

20 Claims, No Drawings

METHODS AND COMPOSITIONS FOR REDUCING FALSE POSITIVE SIGNALS IN AN RNA AMPLIFICATION SYSTEM

BACKGROUND

Q Beta (Qβ) replicase is a template specific RNA directed RNA polymerase derived from the bacteriophage Qβ. In vivo, the normal function of Qβ replicase is to replicate the RNA genome of the Qβ bacteriophage to produce progeny phage genomes. The Qβ virion contains one molecule of single stranded RNA which is termed the viral plus strand. This is a strand utilized as mRNA to direct viral protein synthesis. The Qβ replicase enzyme uses this plus strand as the template to produce RNA copies which are complementary to the original template. These RNA molecules are termed minus strands.

Importantly, both the plus and minus strands are templates for the enzyme. Therefore, the replication of the RNA template proceeds in an exponential fashion. Thus, a few molecules of the replicatable RNA template are replicated in an exponential fashion so long as the enzyme is present in molar excess.

The enzyme also has the capacity to replicate certain RNA and DNA templates in vitro. One well studied example of such an RNA template is the MDV-1 RNA (Mills et al., Science 180:916–927 (1973)). The amplification of MDV-1 DNA by the enzyme Qβ replicase has been disclosed, for example in published European Patent Application 91309430.6 (publication number 0 481 704 A1). Under conditions appropriate for replication, each round of replication takes approximately 15 seconds. Under these conditions, a single MDV-1 molecule will yield $10^{12}$ progeny strands in only thirteen minutes (Pritchard and Stefano, *Ann. Biol. Clin.* 48:492–497 (1990)). This is an amount of RNA which is easily detectable by conventional methods such as fluorescence.

Additional nucleic acid sequences may be joined to the Qβ replicase template sequences to generate a recombinant template which is useful as a hybridization probe for the detection of a target nucleic acid sequence in a sample. In general, the additional nucleic acid sequence can be embedded at tolerant positions within the replicatable RNA or DNA sequence (see e.g., Miele et al., *J. Mol. Biol.* 171: 281–295 (1983)), or it can be added to either the 5' or 3' end of the replicatable template molecule (see e.g., U.S. Pat. No. 5,112,734). Either of these embodiments are useful in conventional hybridization methods.

Typically, such hybridization methods require that nucleic acids from an experimental sample be fixed to a solid support (e.g., nitrocellulose or nylon membranes). The replicatable nucleic acid sequence, having the additional probe sequence attached, is contacted with the support bound nucleic acids under conditions appropriate for hybridization. After removing non-specifically bound nucleic acid by conventional methods, the Qβ replicase system is used to amplify specifically bound replicatable template sequences. The replication of the template molecule in the sample is an indication of the presence of the target nucleic acid in the sample.

The sensitivity of this system, however, is limited due to the generation of "background signal" or "false positives". Typically, preparations of Qβ replicase contain endogenous replicatable RNA species. When such a preparation of Qβ replicase is incubated near neutral pH in the presence of nucleoside triphosphates and magnesium ions, but without exogenously added template RNA, the endogenous replicatable RNA species is amplified exponentially. Using commonly employed detection methods (e.g. fluorescence), this amplified endogenous species would be indistinguishable from the amplified product of a recombinant template of the type described above. The detection of this endogenous species in a hybridization assay in which an exogenous RNA template containing a probe sequence has been added to detect the presence of a target nucleic acid sequence results in the identification of false positives.

The endogenous replicatable RNA species which gives rise to the false positives is extremely difficult to completely remove in the process of preparing a Qβ replicase enzyme batch. Although methods have been reported which can be used to prepare an enzyme batch which does not contain an endogenous species (see e.g., U.S. Ser. No. 07/364,306, filed on Jun. 9, 1989, even such methods are known to exhibit batch to batch variability with respect to the endogenous species.

In addition to Qβ replicase, other enzymes are known to have an RNA dependent RNA polymerase activity. For example, the DNA dependent RNA polymerase from coliphage T7 is known to replicate certain small RNA molecules in a manner analogous to Qβ replicase (see e.g., Konarska and Sharp, *Cell* 63:609–618 (1990)). Application of T7 RNA polymerase to assays similar to those described above is very likely to involve analogous false positive problems. Indeed it is possible that the known RNA substrates for T7 RNA polymerase arose originally in cells which were a source of the enzyme and that these or other such substrates could give rise to false positive results in assays based on RNA amplification by T7 RNA polymerase (or any other enzyme having an RNA dependent RNA polymerase activity). A method for addressing this problem of false positives in an amplification assay would represent a clear advance in the art.

SUMMARY OF THE INVENTION

This invention relates to an improved method for detecting the presence of a replicatable template molecule in a sample, the template molecule being replicatable by an RNA or DNA directed RNA polymerase. The method employs an RNA polymerase enzyme preparation which has been pretreated with a ribonuclease. Although the method can be applied to any RNA or DNA directed RNA polymerase, in a preferred embodiment, the RNA polymerase is the enzyme Qβ replicase. The ribonuclease treated enzyme preparation is contacted with a sample which is to be tested for the presence of the replicatable template molecule, under conditions appropriate for replication. The presence of the amplified template molecule is detected as an indication of the presence of a replicatable template molecule in the sample.

When used in hybridization experiments, an additional nucleic acid sequence (or sequences) is attached to the replicatable template molecule. This additional nucleic acid sequence, referred to herein as a probe sequence, is complementary to a target nucleic acid sequence. In a preferred embodiment, the probe sequence is attached to the 5' or 3' end of the replicatable template.

The invention also relates to a ribonuclease treated RNA or DNA directed RNA polymerase preparation which is substantially free of contamination by replicatable template species. In a preferred embodiment, the RNA polymerase is the enzyme Qβ replicase.

DETAILED DESCRIPTION OF THE INVENTION

The subject invention relates to an improved method for amplifying a replicatable RNA or DNA template molecule using an RNA or DNA directed RNA polymerase such as the enzyme Qβ replicase "Amplifying" as used herein, means "increasing the concentration of". More specifically, the improvement relates to the reduction or elimination of false positive signals which result from the presence of an endogenous replicatable template species in the RNA polymerase enzyme preparation. In addition, the teaching of this invention can also be used to remove contaminating template species which may have been inadvertently introduced into the enzyme preparation but which are not endogenous per se. As discussed briefly in the background section above, the presence of such undesirable replicatable RNA species is a common problem. When, for example, a Qβ replicase preparation containing such template molecules is used to amplify an exogenous replicatable RNA, multiple replicatable species are produced in the amplification reaction. In a common situation, the exogenous replicatable RNA is a recombinant RNA containing a probe sequence which is complementary to a target nucleic acid. Many of the most convenient methods for monitoring amplification cannot distinguish between the amplified products of an endogenous or contaminating species, and a specific, exogenously added probe species. Therefore, the detection of a replicatable species, under these circumstances, cannot simply be correlated with the specific binding of a probe sequence to a target nucleic acid without additional experimentation.

The invention is based on the discovery that the treatment of an RNA or DNA directed RNA polymerase preparation with a ribonuclease is effective in eliminating false positives by hydrolyzing the endogenous or contaminating replicatable species found in the enzyme preparation. Subsequently added template molecules, which are relatively resistant to RNAase digestion, are amplifiable using the ribonuclease treated enzyme preparation.

The ribonucleases are enzymes which hydrolyze RNA. The ribonucleases can be classified in two broad groups, endonucleases and exonucleases. The endonucleases cleave phosphodiester bonds within an RNA molecule whereas exonucleases remove monomers from the termini of an RNA molecule in either a random or processive manner.

In the Exemplification which follows, pancreatic ribonuclease A was employed to reduce or eliminate false positive signals. In theory any ribonuclease can be used to reduce false positives in a Qβ replicase amplification system. In order to determine conditions appropriate for the use of another ribonuclease, the empirical titration steps discussed below are repeated for the nuclease in question.

As discussed above, the methods of this invention can be used to reduce the frequency of false positive signals in any RNA or DNA directed RNA polymerase amplification system. For convenience, however, the focus of the discussion which follows will be on a particularly well-studied member of this class; the enzyme Qβ replicase. A variety of methods for preparing Qβ replicase have been reported. As a practical matter, it is preferable (although not essential) to prepare a Qβ replicase preparation in such a way as to minimize the content of the contaminating RNA species, prior to treatment with the ribonuclease. Methods have been described which minimize the amount of the contaminating species, and one such method is described in the Exemplification section below.

A first step in determining conditions appropriate for the reduction of false positive signals is to prepare ribonuclease digestion dilution series. The buffering system of the Qβ replicase stock solution to be treated is adjusted according to the requirements of the ribonuclease to be used. The dilution series can be established, for example, in a range of from about 50 ng/ml to about 5 mg/ml. The reaction mixtures are incubated at a temperature, and for a period of time, appropriate for the digestion of the contaminating species in the enzyme preparation.

It is preferable to identify the lowest concentration of ribonuclease which is effective in eliminating the contribution to signal by the contaminating species. By treating the Qβ replicase preparation with the lowest effective concentration of ribonuclease, the amount of residual ribonuclease present in the amplification reaction (which follows the nuclease digestion) is minimized. This is accomplished by incubating aliquots from the various ribonuclease digestion dilution series in a suitable buffer under conditions appropriate for the amplification of a replicatable species by Qβ replicase. No exogenous template is added to this incubation mixture. The amplification of a replicatable species can be monitored using a variety of techniques. A particularly convenient method is to add a fluorescent intercalating agent (e.g., propidium iodide) to the amplification reaction. Such an agent binds to nucleic acid if present in the sample. If bound to a nucleic acid, the agent fluoresces when exposed to light of an appropriate wavelength. Thus, the amplification of nucleic acid in each of the reaction mixtures can be monitored by exposing the reaction mixtures to light of an appropriate wavelength. A control reaction containing an otherwise identical Qβ replicase sample which has not been treated with ribonuclease is established and monitored in parallel. By comparing the results observed with the ribonuclease digestion series to the untreated control, it is easily determined which of the ribonuclease digestions represents the lowest concentration of ribonuclease which is effective in eliminating the contribution to signal by the contaminating species. Because of the variability which may be encountered from batch to batch, these titration experiments should be carried out not only with each new ribonuclease to be tested, but also with each new Qβ replicase batch.

After the titration experiments have been used to identify the minimum concentration appropriate for the elimination of false positives in the Qβ replicase stock solution, it is necessary to determine whether exogenously added template can be amplified using the nuclease treated stock solution. The method of this invention does not require the removal or inactivation of the ribonuclease used to treat the replicase. Thus, in practice an exogenously added replicatable RNA template (e.g., a recombinant RNA probe) will be contacted with a Qβ replicase preparation which contains active ribonuclease.

Although the method of this invention does not require the removal or inactivation of the ribonuclease from the Qβ replicase preparation prior to amplification, convenient and useful methods for inactivation or removal can be developed. For example, micrococcal ribonuclease requires $Ca^{++}$ ions for activity. Thus, micrococcal ribonuclease can be used to digest contaminating replicatable species in a Qβ preparation. A chelator of $Ca^{++}$ (e.g., EGTA) is then added to the replicase preparation prior to the use of the replicase in an amplification reaction. The addition of the chelating agent inactivates the micrococcal nuclease, thereby preventing digestion of the exogenous template in the amplification reaction.

Alternatively, an affinity reagent can be attached to the nuclease, thereby facilitating the removal of the nuclease from the Qβ replicase preparation following the nuclease digestion reaction. An example of such an affinity reagent is biotin. Biotin and avidin are members of a specific binding pair. Thus, a nuclease/biotin conjugate is easily removed from a Qβ replicase preparation by passing the preparation over an avidin affinity column, for example. Other examples of such specific binding pairs are known in the art.

Another alternative method for the removal of the nuclease takes advantage of the purification steps which are used to purify the enzyme from the source organism. Prior to the late stage chromatography steps which are included in most enzyme purification protocols, an RNAase digestion step is carried out for a period of time sufficient to remove any contaminating replicatable RNA species. The RNAase is then removed from the enzyme preparation through the course of the late stage chromatography steps which are necessary to purify the replicase.

To determine whether exogenously added template can be amplified with a ribonuclease treated Qβ replicase preparation, an appropriate quantity of the RNAase treated Qβ replicase stock is diluted (typically 2-10 fold) into a buffered solution containing a known quantity of a suitable template molecule, under conditions appropriate for replication. The progress of the amplification reaction is monitored by conventional methods. The preparation is suitable for use in amplification reactions if a detectable signal is generated. The 2-10 fold dilution may be important in that this effectively decreases the concentration of the ribonuclease significantly. This decrease in concentration may increase the half-life of the exogenous RNA template substantially.

Suitable ribonucleases include pancreatic ribonuclease, micrococcal ribonuclease, T1 ribonuclease and snake venom phosphodiesterase. In addition to the use of the ribonucleases individually to eliminate false positives, mixtures of ribonucleases could be used for the same purpose. Individual ribonucleases exhibit differing specificities. By using a mixture of ribonucleases, RNA present in the solution will be cleaved into smaller fragments thereby decreasing the likelihood that a replicatable species will survive the RNAase treatment. To determine the appropriate concentrations and conditions for the use of a ribonuclease mixture, the titration steps outlined above for use with a single ribonuclease would be carried out.

Thus, one aspect of the invention relates to a method for detecting the presence of a replicatable template molecule in a sample. In one embodiment of the method, the replicatable nucleic acid is attached to a probe sequence which is complementary to a target nucleic acid which is to be detected in a sample. Often, the target nucleic acid will be a bacterial or viral nucleic acid sequence. However, the method is applicable to the detection of any nucleic acid sequence, regardless of the source organism. The replicatable nucleic acid is used to detect the presence of the target nucleic acid in the sample using conventional hybridization techniques followed by amplification with a nuclease treated Qβ replicase preparation.

The MDV-1 molecule exhibits RNAase resistance properties making it a good choice as a replicatable RNA molecule for use in the methods described herein. Not all replicatable RNA molecules exhibit a sufficient degree of RNAase resistance to be useful in the methods of this invention. Whether or not a particular replicatable RNA species is appropriate for use in the methods described herein is easily determined by incubating the RNA species with RNAase and determining whether the molecule is sufficiently resistant to digestion.

Preferably, the probe sequence is attached at the 5' or 3' end of the replicatable RNA molecule or, if the probe is internal, an RNAase resistant variant can be generated and identified by the screening process described below. Typically, the probe sequence is added by generating a DNA construct specifying the desired RNA sequence. The DNA construct contains all regulatory sequences necessary for transcription. The RNA template is generated by contacting the DNA construct with a DNA dependent RNA polymerase under conditions appropriate for transcription. Such a method for generating a recombinant RNA template molecule which is a substrate for Qβ replicase is described in U.S. Pat. No. 5,112,734, issued May 12, 1992. As described in the aforementioned patent, probe sequences attached at either the 3' or 5' end are not replicated by the Qβ replicase enzyme. Thus, with external probe sequences, during the amplification process only the parent RNA template molecule (e.g., MDV-1) is replicated. In contrast, if the probe sequence is inserted internally, the entire recombinant template is replicated by the enzyme. In addition to RNA template molecules, the enzyme Qβ replicase has the ability to amplify DNA template molecules (see e.g., European Patent Application 91309430.6 (publication number 0 481 704 A1)). The reduction of false positions in an assay employing such DNA templates is encompassed by this invention.

As mentioned above, the MDV-1 molecule exhibits excellent RNAase resistance properties. It has been determined that the addition of probe sequences at the 5' or 3' termini does not have a detectable affect on this RNAase resistance property; such molecules tend to exhibit the RNAase resistance properties of the parent molecule.

Internal insertions have also been described in the art (see e.g., Miele et al., *J. Mol. Biol.* 171:281–295 (1983)). However, it has been determined that internal insertions have a tendency to render the recombinant RNA molecule more susceptible to RNAase digestion. If the probe portion is to be located at an internal site within the replicatable RNA, precautions must be taken in an effort to ensure stability.

One approach which is useful for identifying RNAase resistant recombinant molecules having the probe portion embedded at an internal site within the parent RNA sequence involves the addition of random nucleotide sequences at the 5' and 3' termini of the probe sequence (e.g., flanked by MDV sequences). These random nucleotide sequences can be added by generating a DNA construct which specifies the random sequences at the termini, and transcribing RNA from the construct as described above. Typically each random terminal extension is about ½ the length of the probe portion. A library of such molecules bearing differing extensions at these termini is generated by conventional cloning techniques. The library is screened for RNAase resistant recombinant molecules, and those clones demonstrating RNAase resistance are suitable for use in the methods of this invention.

The subject invention also relates to a Qβ replicase enzyme preparation which is treated with a ribonuclease. Preferably, the replicase preparation is substantially free of contamination by a replicatable RNA species. A preparation which is substantially free of contamination by a replicatable RNA species is a preparation which, when incubated under conditions appropriate for amplification, will not produce a replicatable RNA species unless an exogenous template is added.

EXEMPLIFICATION

Purification of Q Beta Replicase from Phage-Infected E. coli Cells

One hundred (100 g) grams of recombinant *E. coli* cells containing the cloned gene for the Qβ replicase phage subunit under the control of the lambda P1 promoter was used as the source of Qβ replicase. The following procedure was carried out in a cold room (4° C.), and in an RNA-free environment, using sterile buffers to minimize contamination with MDV-1 RNA. The *E. coli* cells were suspended in a one liter beaker in 2.5 volumes of a solution containing 50 mM Tris-HCl buffer, (pH 7.8), 55 mM $MgCl_2$, 5 mM 2-mercaptoethanol, 1 mM EDTA and 500 mM NaCl. One half of the cell suspension was transferred to a Rosett sonicating cell (250 ml, Heat Systems-Ultrasonics) and the cell was placed in an ice-water bath. The remainder of the cell suspension was kept on ice. The cell suspension was sonicated 4 times, 2 minutes each time, at an output control setting of 7. After each 2 minute interval, the temperature of the suspension increased from 4° C. to about 10°–12° C. The cell suspension was allowed to cool down to 6° C. or less before resuming sonication. After sonication was complete, the volume of the sonicated cell suspension was measured. The suspension was transferred to a clean 1 L beaker and placed on ice. The procedure was repeated with the remainder of the cell suspension.

The sonicated cell suspension was stirred on a stir plate at 4° C. 0.03 volumes of 10% polyethyleneimine (w/v) was then gradually added to the cell homogenate. After all the polyethyleneimine was added, the suspension was stirred for an additional 15 minutes. The suspension was then centrifuged for 30 minutes at 10,000 rpm at 4° C. The clear supernatant was measured and transferred to a clean 2 L beaker.

The supernatant was diluted with 4 volumes of 50 mM Tris- HCl (pH 7.8) 5 mM $MgCl_2$, 5 mM 2-mercaptoethanol, 1 mM EDTA, and applied in a concentration of 30 mg of protein per ml of resin to an equilibrated 220 ml Q Sepharose column (Q Sepharose Fast Flow resin, Pharmacia) at a flow rate of 400–450 ml/hr. A UV-1 monitor (Pharmacia, 280 nm filter) was set at an AUFS of 2.0 and the chart speed of 0.2 mm/min. While the enzyme was being loaded onto the column, the supernatant fraction was assayed for Q Beta replicase activity using the Poly C template assay.

The Poly C template assay was carried out by mixing the following reagents in a 1.5 ml micro-centrifuge tube at room temperature:

---
5 μl of 5 × Q beta replicase buffer (450 MM Tris-HCl, (pH 7.8), and 70 MM $MgCl_2$).
5 μl of 1.0 mg/ml Poly C
1 μl of 10 mM GTP
1 μl of 50 μg/ml Rifampicin
0.5 μl of alpha-$^{32}$P GTP, 10 μCi/μl
11.5 μl DEPC treated water
1 μl of enzyme 25 μl total volume
---

The reaction mixture was incubated for 10 minutes at 37° and 10 μl aliquots were removed from each reaction tube and pipetted onto DE-81 filters (Whatman). The filters were air dried for 1–2 minutes. From one of the reaction tubes, 10 μl was removed and pipetted onto a DE-81 filter, allowed to air dry, placed in a scintillation vial containing 3 ml of water and counted. From this data the total number of counts that were added to each tube could be determined.

The filters were transferred to a 1 L beaker containing 200 ml of sodium phosphate (500 mM, pH 7.4) wash buffer. The filters were washed for 20 minutes at room temperature with occasional shaking. The wash solution was decanted and an additional 200 ml of fresh wash buffer solution was added to the beaker and the filters were washed again. The wash step was for 20 minutes. The buffer was removed, and repeated one more time. After the third wash, 200 ml of distilled, deionized water was added to the beaker and the filters were washed for 10 minutes with mixing.

The filters were removed from the water and blotted dry on a piece of Whatman 3 mm paper. The filters then were transferred to scintillation vials (Wheaton) containing 3 ml of water. The vials were capped and the radioactivity in each vial was determined in a scintillation counter at settings for detection of $^{32}$P, to determine the level of incorporation by each fraction.

After the entire enzyme preparation had been loaded onto the column, the column was washed with a solution of 50 mM Tris-HCl (pH 7.8), 5 mM $MgCl_2$, 5 mM 2-mercaptoethanol, 1 mM EDTA, and 100 mM NaCl, at a flow rate of 400–450 ml/hr. The column was washed until the UV absorbance decreased to less than 0.4 (4–6 column volumes).

A 10 column-volume (2×1100 ml) gradient was prepared, ranging from 100–400 mM NaCl in 50 mM Tris-HCl (pH 7.8), 5 mM $MgCl_2$, 5 mM 2-mercaptoethanol, 1 mM EDTA. The gradient was run at a flow rate of 200–225 ml/hr and fractions of 22 ml were collected. To minimize the risk of contaminating the fractions with MDV RNA, 0.1–0.2 ml aliquots of the fractions to be assayed were removed using sterile 1 ml pipettes and transferred to sterile 1.5 ml microcentrifuge tubes. The Q Sepharose fractions were assayed for Q Beta replicase activity using the Poly C assay described above.

The peak replicase fractions were assayed for the presence of contaminating RNAase, and for activity in the absence of added template. The peak Qβ replicase fractions were those fractions that contain 50% +/−5% of the activity of the maximum fraction, are free of major RNAase contamination and are substantially free of contamination by a replicatable RNA species. Fractions meeting these criteria were pooled. The protein concentration of the fractions were determined using the Bradford Assay. Replicase activity was determined using the Poly C assay.

An S Sepharose (Pharmacia) column was prepared and equilibrated with 10 column volumes of 50 mM Tris-HCl (pH 7.8) 5 mM $MgCl_2$, 5 mM 2-mercaptoethanol, 1 mM EDTA. The diluted enzyme was applied to the column in a concentration of 10 mg of protein per ml of resin at a flow rate of two column volumes per hour. The UV-1 monitor was set at an AUFS setting of 0.5 and the chart speed at 0.2 mm/min.

The enzyme preparation was applied to the column, and the column was washed with 50 mM Tris-HCl (pH 7.8), 5 mM $MgCl_2$, 5 mM 2-mercaptoethanol, 1 mM EDTA, and 100 mM NaCl and a 10 column volume gradient of 100 mM to 400 mM NaCl was run at a flow rate of 1 column volume per hour. Fractions of 0.01 volume of the total gradient were collected. 0.1 ml aliquots were removed using sterile 1 ml pipettes and transferred to sterile 1.5 ml microcentrifuge tubes. The S Sepharose fractions were assayed for replicase activity using the Poly C assay to define the location of the replicase peak. To discriminate between the enzyme fractions which contain Q Beta "Holoenzyme" versus those that contain Q Beta "alpha-less" enzyme which does not have the S1 subunit and cannot replicate MDV RNA templates, aliquots of the peak fraction were run on denaturing 10–15% polyacrylamide gels using the PhastSystem (Pharmacia).

Fractions containing the highest replicase activity were assayed for the presence of contaminating RNAase, and were assayed in the absence of any added template to determine whether any of the peak fraction contained contaminating RNA species. The "peak" fractions were those fractions that contain at least 33% +/–5% of the activity of the maximum fraction, only Q Beta "Holoenzyme" that are substantially free of RNAase contamination and that are substantially free of MDV-1 RNA.

Fractions meeting all of these criteria were pooled. The protein concentration of this fraction was determined using the Bradford Assay. Replicase activity was determined using the Poly C assay. The fraction was also assayed for replicase activity using MDV RNA as a template. An equal volume of chilled ultra pure glycerol was added to the remainder of the fraction, and mixed gently until no Schleiren lines were observed.

Effect of RNAse Treatment on RNA Synthesis Absent Exogenous Template

The preparation method described above can result in some variability with respect to contamination by a replicatable species. The synthesis of a replicatable RNA in the absence of exogenous template is referred to herein as a "false positive". In one enzyme preparation, a high false positive rate was observed in amplification reactions done at 10 mM $Mg^{++}$. This preparation was selected to test the effect of RNAase by Qβ replicase.

Bovine pancreatic ribonuclease was added to the Qβ replicase stock solution at various concentrations ranging from 0 to 4 μg/ml. The Qβ replicase stock solution was 25 mM Tris/HCl (pH 7.8), 5 mM $MgCl_2$, 50 mM NaCl and 50% glycerol. The various stock solutions were incubated at 37° C. for 60 minutes and then stored at 4° C.

Aliquots of each of these stored stock solutions were subsequently diluted into reaction buffer, the final composition of which is:

110 mM Tris/HCl (pH 7.8);

0.6 mM each ATP, CTP, GTP, UTP;

$MgCl_2$ 10 mM; and

Propidium iodide 1 μg/ml.

Table 1 represents the results of experiments designed to measure elapsed times (minutes) for the appearance of false positives using Q-beta replicase pre-treated with various amounts of ribonuclease. The concentration of the nuclease in the digestion reaction is shown at the top of each column.

The data shown in Table 1 was generated by incubating aliquots of stored stock solutions for 45 minutes at 37° under continuous monitoring for RNA content by propidium iodide fluorescence. The results demonstrate that untreated aliquots of Qβ replicase had a false positive rate of 21/24 with signal appearing at times ranging from 7.24 to 35.53 minutes (Table 1, column 7).

Gradually increasing the concentration of ribonuclease to which replicase was exposed resulted in a decreased number of false positives. For example column 4 of Table 1 presents data for replicase pretreated with 250 ng/ml RNAase. The false positive rate is reduced to 7/24. Further increase in RNAase concentration to 1000 ng/ml reduced the false positive rate to 0/24. (Table 1, column 3).

Amplification of Exogenous Template with RNAase Treated Stock

The results discussed above demonstrate that ribonuclease digestion can abolish false positives which are attributable contamination with a replicatable RNA species. However it was not possible to predict whether residual ribonuclease would interfere with the amplification of an exogenous RNA template. The RNAase enzymes are notoriously difficult to inactivate and harsh inactivation methods are inappropriate for a preparation of Qβ replicase. The effect of ribonuclease on the amplification of exogenous template was tested by pretreating the Qβ replicase with various amounts of ribonuclease and subsequently assaying for various numbers of added template molecules. A tenfold dilution series of replicatable template molecules, starting at 1,000,000 per reaction and going down to 1 molecule per reaction was assayed with Qβ replicase which had been pretreated with various amounts of ribonuclease as described above. The assay was run in triplicate. The results are shown in Table 2. In Table 2, individual rows indicate the number of input RNA molecules and columns indicate the RNAase concentration used to treat the Qβ replicase stock solution.

This experiment showed that untreated replicase produced signal from 10 molecules in times ranging from 10.77 to 14.45 minutes. Replicase treated with 1000 ng/ml ribonuclease gave a signal from 10 molecules in 9.48 to 10.35 minutes indicating no decrease in sensitivity. These results demonstrate that the utility of RNAase to reduce the false positive rate in a Qβ replicase assay.

TABLE 1

| 4,000 ng/ml | 2,000 ng/ml | 1,000 ng/ml | 250 ng/ml | 125 ng/ml | 62 ng/ml | 0 ng/ml |
|---|---|---|---|---|---|---|
| ND | ND | ND | ND | 8.42 | 9.9 | 7.24 |
| ND | ND | ND | ND | 8 | 7.85 | 15.51 |
| ND | ND | ND | ND | ND | 5.58 | |
| ND | ND | ND | 26.33 | 8.6 | 9.92 | 30.7 |
| ND | ND | ND | ND | ND | 32.31 | ND |
| ND | ND | ND | 7.05 | 10.15 | 30.75 | 7.36 |
| ND | ND | ND | ND | 28.32 | 21.04 | 11.61 |
| ND | ND | ND | ND | 34.91 | 25.09 | 10.28 |
| ND | ND | ND | ND | 9.71 | 7.2 | 10.74 |
| ND | ND | ND | ND | ND | 10.44 | 26.57 |
| ND | ND | ND | ND | 35.02 | ND | 30.20 |
| ND | ND | ND | ND | 37.41 | 31.16 | 12.67 |
| ND | ND | ND | ND | ND | ND | ND |
| ND | ND | ND | ND | ND | 28.93 | 28.25 |
| ND | ND | ND | 9.42 | ND | 36.87 | 35.53 |
| ND | ND | ND | 8.44 | 12.17 | 30.04 | 32.11 |
| ND | ND | ND | ND | 27.64 | 9.28 | 8.52 |
| ND | ND | ND | 7.28 | 7.13 | 27.35 | 31.75 |
| ND | ND | ND | 7.24 | ND | 6.85 | 24.99 |
| ND | ND | ND | 6.36 | ND | 26.14 | 31.86 |
| ND | ND | ND | ND | 8.66 | 33.67 | ND |
| ND | ND | ND | ND | ND | 33.18 | 33.64 |
| ND | ND | ND | ND | 10.20 | 9.58 | 34.61 |
| ND | ND | ND | ND | 9 | 35.27 | 27.05 |

Table 1: Results of experiments designed to measure elapsed times (minutes) for the appearance of false positives using Q-beta replicase pretreated with various amounts of ribonuclease. The concentration of the nuclease in the digestion reaction is shown at the top of each column. The designation "ND" indicates that signal was "Not Detectable".

TABLE 2

| | No RNAase | | | 2000 ng/ml | | | 1000 ng/ml | | | 500 ng/ml | | |
|---|---|---|---|---|---|---|---|---|---|---|---|---|
| $10^6$ | 4.05 | 3.9 | 3.95 | 4.25 | 3.79 | 4.17 | 4.47 | 3.63 | 3.6 | 3.31 | 3.59 | 3.76 |
| $10^5$ | 4.66 | 4.7 | 4.43 | 4.28 | 4.37 | 4.74 | 4.33 | 4.2 | 4.22 | 3.66 | 4.23 | 4.33 |
| $10^4$ | 5.35 | 5.21 | 5.27 | 5.05 | 4.89 | 5.19 | 5.24 | 4.91 | 4.82 | 5.52 | 4.99 | 4.82 |
| $10^3$ | 5.89 | 6.05 | 6.37 | 5.85 | 5.68 | 5.89 | 5.82 | 5.65 | 5.6 | 5.69 | 4.76 | 4.13 |
| $10^2$ | 7.45 | 8.85 | 7.7 | 7.08 | 8.01 | 7.64 | 7.64 | 7 | 7.54 | 5.05 | 6.37 | 5.41 |
| $10^1$ | 14.45 | 10.97 | 10.77 | 18.62 | 8.93 | 7.57 | 10.05 | 10.35 | 9.48 | 9.54 | 10.36 | 4.12 |
| 1 | ND | ND | ND | ND | ND | 23.68 | 14.2 | 11.8 | ND | 4.85 | ND | 5.19 |
| 0 | ND | ND | ND | ND | ND | ND | ND | ND | ND | 5.57 | ND | 8.41 |

Table 2: Results of experiments testing the effect of ribonuclease on the amplification of exogenous template. Experiments were conducted by pretreating the Qβ replicase with various amounts of ribonuclease and subsequently assaying for various numbers of added template molecules. Individual rows indicate the number of input RNA molecules and columns indicate the RNAase concentration used to treat the Qβ replicase stock solution. The designation "ND" indicates that signal was "Not Detectable".

EQUIVALENTS

Those skilled in the art will recognize, or be able to ascertain using no more than routine experimentation, many equivalents to the specific embodiments described herein. Such equivalents are intended to be encompassed by the following claims.

We claim:

1. A method for detecting the presence of a replicatable template molecule of interest in a sample, comprising the steps of:

a) providing a Qβ replicase enzyme preparation which has been pretreated with a ribonuclease, or a mixture of ribonucleases, under conditions appropriate for the substantial reduction of endogenous or contaminating replicatable template RNA species in the enzyme preparation;

b) contacting a portion of the Qβ replicase enzyme preparation with a sample which is to be tested for the presence of a replicatable template, under conditions appropriate for replication; and c) detecting the presence of amplified template as an indication of the presence of the replicatable template molecule of interest in the sample.

2. A method of claim 1 wherein the ribonuclease is selected from the group consisting of pancreatic ribonuclease, micrococcal nuclease, T1 ribonuclease and snake venom phosphodiesterase.

3. A method of claim 1 wherein the ribonuclease is pancreatic ribonuclease A.

4. A method of claim 3 wherein the concentration of pancreatic ribonuclease A is at least about 125 ng/ml.

5. A method of claim 1 wherein the replicatable template is attached to a probe sequence which is complementary to a target nucleic acid sequence.

6. A method of claim 5 wherein the target nucleic acid sequence is a bacterial or viral nucleic acid sequence.

7. A method for detecting the presence of a heterologous replicatable template molecule of interest in a buffered solution, comprising the steps of:

a) providing a purified Qβ replicase enzyme preparation;

b) treating the purified Qβ replicase enzyme preparation with a ribonuclease under conditions appropriate for the elimination of false positive signals from endogenous or contaminating replicatable template molecules in the enzyme preparation thereby producing a treated enzyme preparation;

c) contacting a portion of the treated enzyme preparation with a buffered solution which is to be tested for the presence of the heterologous replicatable template molecule of interest, under conditions appropriate for replication; and d) detecting the presence of amplified template as an indication of the presence of the heterologous replicatable template molecule of interest in the buffered solution.

8. A method of claim 7 wherein the ribonuclease is selected from the group consisting of pancreatic ribonuclease, micrococcal nuclease, T1 ribonuclease and snake venom phosphodiesterase.

9. A method of claim 7 wherein the replicatable template is attached to a probe sequence which is complementary to a target nucleic acid sequence.

10. A method of claim 9 wherein the target nucleic acid sequence is a bacterial or viral nucleic acid sequence.

11. A method for detecting the presence of a heterologous replicatable template molecule of interest in a buffered solution, comprising the steps of:

a) providing a purified Qβ replicase enzyme preparation;

b) treating the purified Qβ replicase enzyme preparation with a ribonuclease under conditions appropriate for the elimination of false positive signals from endogenous or contaminating replicatable template molecules in the enzyme preparation thereby producing a treated enzyme preparation;

c) removing or inactivating the ribonuclease in the treated enzyme preparation to produce a ribonuclease-free treated enzyme preparation;

d) contacting a portion of the ribonuclease-free treated enzyme preparation with a buffered solution which is to be tested for the presence of a heterologous replicatable template molecule of interest, under conditions appropriate for replication; and e) detecting the presence of amplified template as an indication of the presence of the heterologous replicatable template molecule of interest in the buffered solution.

12. A method of claim 11 wherein the nuclease is micrococcal ribonuclease.

13. A method of claim 14 wherein the micrococcal ribonuclease is inactivated by the addition of EGTA to chelate calcium ions.

14. A method of claim 11 wherein the nuclease is conjugated to an affinity reagent to facilitate removal of the nuclease.

15. A method of claim 14 wherein the ribonuclease is selected from the group consisting of pancreatic ribonuclease, micrococcal nuclease, T1 ribonuclease and snake venom phosphodiesterase.

16. A method of claim 15 wherein the affinity reagent is a member of a specific binding pair.

17. A method of claim 16 wherein the affinity reagent is biotin.

18. A composition comprising:

a) a Qβ replicase enzyme preparation which has been treated with an exogenously added ribonuclease, or a mixture of ribonucleases, under a first set of conditions which are appropriate for the substantial reduction of endogenous or contaminating replicatable template RNA species in the enzyme preparation; said preparation, which contains residual ribonuclease from said treatment, being characterized by yielding no detectable false positive signal of RNA replication following an incubation of about 44 minutes under a second set of conditions which are appropriate for RNA replication but without exogenously added replicatable template RNA; and b) template RNA which has been exogenously added to said enzyme preparation after said ribonuclease treatment and which is replicatable by Qβ replicase under conditions which are appropriate for RNA replication.

19. A composition of claim 18 wherein the enzyme preparation is treated with a ribonuclease selected from the group consisting of pancreatic ribonuclease, micrococcal nuclease, T1 ribonuclease and snake venom phosphodiesterase.

20. A composition of claim 18 wherein the enzyme preparation is treated with pancreatic ribonuclease A.

* * * * *

UNITED STATES PATENT AND TRADEMARK OFFICE
CERTIFICATE OF CORRECTION

PATENT NO. : 5,464,744
DATED : November 7, 1995
INVENTOR(S) : Michael P. Farrell and Juili L. Lin-Goerke It is certified that error appears in the above-indentified patent and that said Letters Patent is hereby corrected as shown below:

In Claim 13, Column 12, Line 59:

Delete "14" and substitute therefor ---12---.

In Claim 18, Column 13, Line 16:

Delete "44" and substitute therefor ---45---.

Signed and Sealed this

Eighteenth Day of June, 1996

*Attest:*

BRUCE LEHMAN

*Attesting Officer*     *Commissioner of Patents and Trademarks*